(12) United States Patent
Eriksen et al.

(10) Patent No.: US 7,943,630 B2
(45) Date of Patent: *May 17, 2011

(54) 3,9-DIAZA-SPIRO[5.5]UNDECANE DERIVATIVES AND THEIR USE AS MONOAMINE NEUROTRANSMITTER RE-UPTAKE INHIBITORS

(75) Inventors: Birgitte L. Eriksen, Farum (DK); Dan Peters, Malmoe (SE); Elsebet Ostergaard Nielsen, Kobenhavn K (DK); John Paul Redrobe, Rødovre (DK)

(73) Assignee: Neurosearch A/S, Ballerup (DK)

( * ) Notice: Subject to any disclaimer, the term of this patent is extended or adjusted under 35 U.S.C. 154(b) by 510 days.

This patent is subject to a terminal disclaimer.

(21) Appl. No.: 11/922,931

(22) PCT Filed: Jun. 28, 2006

(86) PCT No.: PCT/EP2006/063631
§ 371 (c)(1),
(2), (4) Date: Dec. 27, 2007

(87) PCT Pub. No.: WO2007/000463
PCT Pub. Date: Jan. 4, 2007

(65) Prior Publication Data
US 2009/0111841 A1    Apr. 30, 2009

Related U.S. Application Data

(60) Provisional application No. 60/694,678, filed on Jun. 29, 2005.

(30) Foreign Application Priority Data

Jun. 28, 2005 (DK) .................................. 2005 00960

(51) Int. Cl.
*A01N 43/42* (2006.01)
*A61K 31/44* (2006.01)
*C07D 211/00* (2006.01)
*C07D 213/00* (2006.01)
*C07D 215/00* (2006.01)
*C07D 217/00* (2006.01)
*C07D 219/00* (2006.01)
*C07D 221/00* (2006.01)

(52) U.S. Cl. ............................. 514/278; 546/15; 546/16
(58) Field of Classification Search .................. 514/278; 546/15, 16
See application file for complete search history.

(56) References Cited

U.S. PATENT DOCUMENTS 4,041,174 A * 8/1977 Sapse ............................ 514/330
6,288,079 B1   9/2001 Scheel-Kruger et al.

FOREIGN PATENT DOCUMENTS
WO   WO-97/16451 A1   5/1997

OTHER PUBLICATIONS

M. S. Smyth et al, Bioorganic & Medicinal Chemistry Letters Nov. 2001, 1289-1292.

* cited by examiner

*Primary Examiner* — Johann R Richter
*Assistant Examiner* — Samira Jean-Louis
(74) *Attorney, Agent, or Firm* — Birch, Stewart, Kolasch & Birch, LLP

(57) ABSTRACT

This invention relates to novel 3,9-diaza-spiro[5.5]undecane derivatives useful as monoamine neurotransmitter re-uptake inhibitors.
In other aspects the invention relates to the use of these compounds in a method for therapy and to pharmaceutical compositions comprising the compounds of the invention.

12 Claims, No Drawings

3,9-DIAZA-SPIRO[5.5]UNDECANE DERIVATIVES AND THEIR USE AS MONOAMINE NEUROTRANSMITTER RE-UPTAKE INHIBITORS

This application is the National Phase of PCT/EP2006/063631 filed on Jun. 28, 2006, which claims priority under 35 U.S.C. 119(e) to U.S. Provisional Application No. 60/694,678 filed on Jun. 29, 2005 and under 35 U.S.C. 119(a) to Patent Application No. PA 2005 00960 filed in Denmark on Jun. 28, 2005. Both of these prior applications are hereby expressly incorporated by reference into the present application.

TECHNICAL FIELD

This invention relates to novel 3,9-diaza-spiro[5.5]undecane derivatives useful as monoamine neurotransmitter re-uptake inhibitors.

In other aspects the invention relates to the use of these compounds in a method for therapy and to pharmaceutical compositions comprising the compounds of the invention.

BACKGROUND ART

Serotonin Selective Reuptake Inhibitors (SSRIs) currently provide efficacy in the treatment of several CNS disorders, including depression and panic disorder. SSRIs are generally perceived by psychiatrists and primary care physicians as effective, well-tolerated and easily administered. However, they are associated with a number of undesirable features.

Thus, there is still a strong need for compounds with an optimised pharmacological profile as regards the activity on reuptake of the monoamine neurotransmitters serotonin, dopamine and noradrenaline, such as the ratio of the serotonin reuptake versus the noradrenaline and dopamine reuptake activity.

Smyth et al [Smyth M S, Rose J, Mehrotra M M, Heath J, Ruhter G Schotten T, Seroogy J, Volkots D, Pandey A & Scarborough R M; *Bioorganic & Medicinal Chemistry Letters* 2001 11(10) 1289-1292] describe spirocyclic non-peptide glycoprotein IIb-IIIa antagonists. The compounds 4-(3,9-diaza-spiro[5.5]undec-3-yl)-benzonitrile and 3-pyridin-4-yl-3,9-diaza-spiro[5.5]undecane are disclosed; however no pharmaceutical use of these two compounds are disclosed.

SUMMARY OF THE INVENTION

In its first aspect, the invention provides a compound of Formula I:

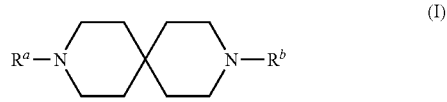

any of its isomers or any mixture of its isomers, or a pharmaceutically acceptable salt thereof,
wherein $R^a$ and $R^b$ are as defined below.

In its second aspect, the invention provides a pharmaceutical composition, comprising a therapeutically effective amount of a compound of the invention, any of its isomers or any mixture of its isomers, or a pharmaceutically acceptable salt thereof, together with at least one pharmaceutically acceptable carrier, excipient or diluent.

In a further aspect, the invention provides the use of a compound of the invention, any of its isomers or any mixture of its isomers, or a pharmaceutically acceptable salt thereof, for the manufacture of a pharmaceutical composition for the treatment, prevention or alleviation of a disease or a disorder or a condition of a mammal, including a human, which disease, disorder or condition is responsive to inhibition of monoamine neurotransmitter re-uptake in the central nervous system.

In a still further aspect, the invention relates to a method for treatment, prevention or alleviation of a disease or a disorder or a condition of a living animal body, including a human, which disorder, disease or condition is responsive to inhibition of monoamine neurotransmitter re-uptake in the central nervous system, which method comprises the step of administering to such a living animal body in need thereof a therapeutically effective amount of a compound of the invention, any of its isomers or any mixture of its isomers, or a pharmaceutically acceptable salt thereof.

Other objects of the invention will be apparent to the person skilled in the art from the following detailed description and examples.

DETAILED DISCLOSURE OF THE INVENTION

3,9-diaza-spiro[5.5]undecane Derivatives

In its first aspect the present invention provides compounds of formula I:

any of its isomers or any mixture of its isomers,
or a pharmaceutically acceptable salt thereof;
wherein
$R^a$ represents hydrogen or alkyl;
  which alkyl is optionally substituted with one or more substituents independently selected from the group consisting of:
    halo, trifluoromethyl, trifluoromethoxy, cyano, hydroxy, amino, nitro, alkoxy, cycloalkoxy, alkyl, cycloalkyl, cycloalkylalkyl, alkenyl and alkynyl; and
$R^b$ represents an aryl or a heteroaryl group,
  which aryl or heteroaryl group is optionally substituted with one or more substituents independently selected from the group consisting of:
    halo, trifluoromethyl, trifluoromethoxy, cyano, nitro, hydroxy, alkoxy, cycloalkoxy, alkoxyalkyl, cycloalkoxyalkyl, methylenedioxy, ethylenedioxy, alkyl, cycloalkyl, cycloalkylalkyl, alkenyl, alkynyl, —NR'R", —(C=O)NR'R" or —NR'(C=O)R";
      wherein R' and R" independent of each other are hydrogen or alkyl; with the proviso that the compound is not
4-(3,9-diaza-spiro[5.5]undec-3-yl)-benzonitrile or
3-pyridin-4-yl-3,9-diaza-spiro[5.5]undecane.

In one embodiment, $R^a$ represents hydrogen or alkyl. In a special embodiment, $R^a$ represents hydrogen. In a further embodiment, $R^a$ represents alkyl, such as methyl.

In a still further embodiment, $R^b$ represents a phenyl group, which phenyl group is optionally substituted with one or more substituents independently selected from the group consisting of: halo, trifluoromethyl, trifluoromethoxy, cyano and alkoxy.

In a further embodiment, $R^b$ represents a phenyl group, which phenyl group is substituted once with a substituent selected from the group consisting of: halo, trifluoromethyl, trifluoromethoxy, cyano and alkoxy.

In a special embodiment, $R^b$ represents halophenyl, such as chlorophenyl, such as 4-chlorophenyl.

In a further embodiment, $R^b$ represents a phenyl group, which phenyl group is substituted twice with substituents independently selected from the group consisting of: halo, trifluoromethyl, trifluoromethoxy, cyano and alkoxy.

In a special embodiment, $R^b$ represents dihalophenyl, such as dichlorophenyl, such as 2,3-dichlorophenyl or 3,4-dichlorophenyl. In a further embodiment, $R^b$ represents chlorofluorophenyl, such as 3-chloro-4-fluoro-phenyl In a still further embodiment, $R^b$ represents a naphthyl group, which naphthyl group is optionally substituted with one or more substituents independently selected from the group consisting of: halo, trifluoromethyl, trifluoromethoxy, cyano and alkoxy.

In a special embodiment, $R^b$ represents alkoxynaphthyl, such as methoxynaphthyl, such as 6-methoxy-naphthalen-2-yl. In a further embodiment, $R^b$ represents naphthyl, such as naphthalen-2-yl.

In a further embodiment, $R^b$ represents a pyridyl group, which pyridyl group is optionally substituted with one or more substituents independently selected from the group consisting of: halo, trifluoromethyl, trifluoromethoxy, cyano and alkoxy.

In a special embodiment, $R^b$ represents halopyridyl, such as 5-halo-pyridin-2-yl or 6-halo-pyridin-2-yl, such as 5-chloro-pyridin-2-yl, 5-bromo-pyridin-2-yl, 6-chloro-pyridin-2-yl or 6-bromo-pyridin-2-yl.

In a special embodiment the compound of the invention is
3-(3,4-Dichloro-phenyl)-9-methyl-3,9-diaza-spiro[5.5]undecane;
3-(6-Chloro-pyridin-2-yl)-9-methyl-3,9-diaza-spiro[5.5]undecane;
3-(6-Chloro-pyridin-2-yl)-3,9-diaza-spiro[5.5]undecane;
3-(5-Chloro-pyridin-2-yl)-3,9-diaza-spiro[5.5]undecane;
3-(6-Methoxy-naphthalen-2-yl)-3,9-diaza-spiro[5.5]undecane;
3-(3,4-Dichloro-phenyl)-3,9-diaza-spiro[5.5]undecane;
3-(6-Bromo-pyridin-2-yl)-3,9-diaza-spiro[5.5]undecane;
3-(2,3-Dichloro-phenyl)-3,9-diaza-spiro[5.5]undecane;
3-(4-Chloro-phenyl)-3,9-diaza-spiro[5.5]undecane;
3-(3-Chloro-4-fluoro-phenyl)-3,9-diaza-spiro[5.5]undecane;
3-(5-Bromo-pyridin-2-yl)-3,9-diaza-spiro[5.5]undecane;
3-Naphthalen-2-yl-3,9-diaza-spiro[5.5]undecane;
3-(6-Methoxy-naphthalen-2-yl)-9-methyl-3,9-diaza-spiro[5.5]undecane;
or a pharmaceutically acceptable salt thereof.

Any combination of two or more of the embodiments as described above is considered within the scope of the present invention.

Definition of Substituents

In the context of this invention halo represents fluoro, chloro, bromo or iodo.

In the context of this invention an alkyl group designates a univalent saturated, straight or branched hydrocarbon chain. The hydrocarbon chain preferably contains of from one to six carbon atoms ($C_{1-6}$-alkyl), including pentyl, isopentyl, neopentyl, tertiary pentyl, hexyl and isohexyl. In a preferred embodiment alkyl represents a $C_{1-4}$-alkyl group, including butyl, isobutyl, secondary butyl, and tertiary butyl. In another preferred embodiment of this invention alkyl represents a $C_{1-3}$-alkyl group, which may in particular be methyl, ethyl, propyl or isopropyl.

In the context of this invention an alkenyl group designates a carbon chain containing one or more double bonds, including di-enes, tri-enes and poly-enes. In a preferred embodiment the alkenyl group of the invention comprises of from two to six carbon atoms ($C_{2-6}$-alkenyl), including at least one double bond. In a most preferred embodiment the alkenyl group of the invention is ethenyl; 1- or 2-propenyl; 1-, 2- or 3-butenyl, or 1,3-butadienyl; 1-, 2-, 3-, 4- or 5-hexenyl, or 1,3-hexadienyl, or 1,3,5-hexatrienyl.

In the context of this invention an alkynyl group designates a carbon chain containing one or more triple bonds, including di-ynes, tri-ynes and poly-ynes. In a preferred embodiment the alkynyl group of the invention comprises of from two to six carbon atoms ($C_{2-6}$-alkynyl), including at least one triple bond. In its most preferred embodiment the alkynyl group of the invention is ethynyl; 1-, or 2-propynyl; 1-, 2-, or 3-butynyl, or 1,3-butadiynyl; 1-, 2-, 3-, 4-pentynyl, or 1,3-pentadiynyl; 1-, 2-, 3-, 4-, or 5-hexynyl, or 1,3-hexadiynyl or 1,3,5-hexatriynyl.

In the context of this invention a cycloalkyl group designates a cyclic alkyl group, preferably containing of from three to seven carbon atoms ($C_{3-7}$-cycloalkyl), including cyclopropyl, cyclobutyl, cyclopentyl, cyclohexyl and cycloheptyl.

Alkoxy is O-alkyl, wherein alkyl is as defined above.

Cycloalkoxy means O-cycloalkyl, wherein cycloalkyl is as defined above.

Cycloalkylalkyl means cycloalkyl as above and alkyl as above, meaning for example, cyclopropylmethyl.

In the context of this invention an aryl group designates a carbocyclic aromatic ring system such as phenyl, naphthyl or fluorenyl.

In the context of this invention a heteroaryl group designates an aromatic mono- or bicyclic heterocyclic group, which holds one or more heteroatoms in its ring structure. Preferred heteroatoms include nitrogen (N), oxygen (O), and sulphur (S).

Preferred monocyclic heteroaryl groups of the invention include aromatic 5- and 6-membered heterocyclic monocyclic groups, including for example, but not limited to, oxazolyl, isoxazolyl, thiazolyl, isothiazolyl, tetrazolyl, 1,2,4-oxadiazolyl, 1,2,5-oxadiazolyl, triazolyl, 1,2,4-thiadiazolyl, 1,2,5-thiadiazolyl, imidazolyl, pyrrolyl, pyrazolyl, furanyl, thienyl, pyridyl, pyrimidyl, or pyridazinyl.

Preferred bicyclic heteroaryl groups of the invention include for example, but not limited to, indolizinyl, indolyl, isoindolyl, indazolyl, benzofuranyl, benzo[b]thienyl, benzimidazolyl, benzoxazolyl, benzooxadiazole, benzothiazolyl, benzo[d]isothiazolyl, purinyl, quinolinyl, isoquinolinyl, cinnolinyl, phthalazinyl, quinazolinyl, quinoxalinyl, 1,8-naphthyridinyl, pteridinyl, and indenyl. Included in the bicyclic heteroaryl group is also coumarinyl.

Pharmaceutically Acceptable Salts

The chemical compound of the invention may be provided in any form suitable for the intended administration. Suitable forms include pharmaceutically (i.e. physiologically) acceptable salts, and pre- or prodrug forms of the chemical compound of the invention.

Examples of pharmaceutically acceptable addition salts include, without limitation, the non-toxic inorganic and organic acid addition salts such as the hydrochloride, the hydrobromide, the nitrate, the perchlorate, the phosphate, the sulphate, the formate, the acetate, the aconate, the ascorbate, the benzenesulphonate, the benzoate, the cinnamate, the citrate, the embonate, the enantate, the fumarate, the glutamate, the glycolate, the lactate, the maleate, the malonate, the mandelate, the methanesulphonate, the naphthalene-2-sulphonate, the phthalate, the salicylate, the sorbate, the stearate, the succinate, the tartrate, the toluene-p-sulphonate, and the like. Such salts may be formed by procedures well known and described in the art.

Other acids such as oxalic acid, which may not be considered pharmaceutically acceptable, may be useful in the preparation of salts useful as intermediates in obtaining a chemical compound of the invention and its pharmaceutically acceptable acid addition salt.

Examples of pharmaceutically acceptable cationic salts of a chemical compound of the invention include, without limitation, the sodium, the potassium, the calcium, the magnesium, the zinc, the aluminium, the lithium, the choline, the lysinium, and the ammonium salt, and the like, of a chemical compound of the invention containing an anionic group. Such cationic salts may be formed by procedures well known and described in the art.

In the context of this invention the "onium salts" of N-containing compounds are also contemplated as pharmaceutically acceptable salts. Preferred "onium salts" include the alkyl-onium salts, the cycloalkyl-onium salts, and the cycloalkylalkyl-onium salts.

Examples of pre- or prodrug forms of the chemical compound of the invention include examples of suitable prodrugs of the substances according to the invention include compounds modified at one or more reactive or derivatizable groups of the parent compound. Of particular interest are compounds modified at a carboxyl group, a hydroxyl group, or an amino group. Examples of suitable derivatives are esters or amides.

The chemical compound of the invention may be provided in dissoluble or indissoluble forms together with a pharmaceutically acceptable solvent such as water, ethanol, and the like. Dissoluble forms may also include hydrated forms such as the monohydrate, the dihydrate, the hemihydrate, the trihydrate, the tetrahydrate, and the like. In general, the dissoluble forms are considered equivalent to indissoluble forms for the purposes of this invention.

Steric Isomers

It will be appreciated by those skilled in the art that the compounds of the present invention exist in different stereoisomeric forms—including enantiomers, diastereomers and cis-trans-isomers.

The invention includes all such isomers and any mixtures thereof including racemic mixtures.

Racemic forms can be resolved into the optical antipodes by known methods and techniques. One way of separating the enantiomeric compounds (including enantiomeric intermediates) is—in the case the compound being a chiral acid—by use of an optically active amine, and liberating the diastereomeric, resolved salt by treatment with an acid. Another method for resolving racemates into the optical antipodes is based upon chromatography on an optical active matrix. Racemic compounds of the present invention can thus be resolved into their optical antipodes, e.g., by fractional crystallisation of D- or L- (tartrates, mandelates, or camphorsulphonate) salts for example.

The chemical compounds of the present invention may also be resolved by the formation of diastereomeric amides by reaction of the chemical compounds of the present invention with an optically active activated carboxylic acid such as that derived from (+) or (−) phenylalanine, (+) or (−) phenylglycine, (+) or (−) camphanic acid or by the formation of diastereomeric carbamates by reaction of the chemical compound of the present invention with an optically active chloroformate or the like.

Additional methods for the resolving the optical isomers are known in the art. Such methods include those described by Jaques J, Collet A, & Wilen S in "*Enantiomers, Racemates, and Resolutions*", John Wiley and Sons, New York (1981).

Optical active compounds can also be prepared from optical active starting materials or intermediates.

Labelled Compounds

The compounds of the invention may be used in their labelled or unlabelled form. In the context of this invention the labelled compound has one or more atoms replaced by an atom having an atomic mass or mass number different from the atomic mass or mass number usually found in nature. The labelling will allow easy quantitative detection of said compound.

The labelled compounds of the invention may be useful as diagnostic tools, radio tracers, or monitoring agents in various diagnostic methods, and for in vivo receptor imaging.

The labelled isomer of the invention preferably contains at least one radionuclide as a label. Positron emitting radionuclides are all candidates for usage. In the context of this invention the radionuclide is preferably selected from $^2H$ (deuterium), $^3H$ (tritium), $^{13}C$, $^{14}C$, $^{131}I$, $^{125}I$, $^{123}I$, and $^{18}F$.

The physical method for detecting the labelled isomer of the present invention may be selected from Position Emission Tomography (PET), Single Photon Imaging Computed Tomography (SPECT), Magnetic Resonance Spectroscopy (MRS), Magnetic Resonance Imaging (MRI), and Computed Axial X-ray Tomography (CAT), or combinations thereof.

Methods of Preparation

The chemical compounds of the invention may be prepared by conventional methods for chemical synthesis, e.g. those described in the working examples. The starting materials for the processes described in the present application are known or may readily be prepared by conventional methods from commercially available chemicals.

Also one compound of the invention can be converted to another compound of the invention using conventional methods.

The end products of the reactions described herein may be isolated by conventional techniques, e.g. by extraction, crystallisation, distillation, chroma-tography, etc.

Biological Activity

Compounds of the invention may be tested for their ability to inhibit reuptake of the monoamines dopamine, noradrenaline and serotonin in synaptosomes e.g. such as described in WO 97/30997. Based on the balanced activity observed in these tests the compound of the invention is considered useful for the treatment, prevention or alleviation of a disease or a disorder or a condition of a mammal, including a human, which disease, disorder or condition is responsive to inhibition of monoamine neurotransmitter re-uptake in the central nervous system.

In a special embodiment, the compounds of the invention are considered useful for the treatment, prevention or alleviation of: mood disorder, depression, atypical depression, depression secondary to pain, major depressive disorder, dysthymic disorder, bipolar disorder, bipolar I disorder, bipolar II disorder, cyclothymic disorder, mood disorder due to a general medical condition, substance-induced mood disorder, pseudodementia, Ganser's syndrome, obsessive compulsive disorder, panic disorder, panic disorder without agoraphobia, panic disorder with agoraphobia, agoraphobia without history of panic disorder, panic attack, memory deficits, memory loss, attention deficit hyperactivity disorder, obesity, anxiety, generalized anxiety disorder, eating disorder, Parkinson's disease, parkinsonism, dementia, dementia of ageing, senile dementia, Alzheimer's disease, acquired immunodeficiency syndrome dementia complex, memory dysfunction in ageing, specific phobia, social phobia, social anxiety disorder, post-traumatic stress disorder, acute stress disorder, drug addiction, drug abuse, cocaine abuse, nicotine abuse, tobacco abuse, alcohol addiction, alcoholism, kleptomania, pain, chronic pain, inflammatory pain, neuropathic pain, migraine pain, tension-type headache, chronic tension-type headache, pain associated with depression, fibromyalgia, arthritis, osteoarthritis, rheumatoid arthritis, back pain, cancer pain, irritable bowel pain, irritable bowel syndrome, post-operative pain, post-mastectomy pain syndrome (PMPS), post-stroke pain, drug-induced neuropathy, diabetic neuropathy, sympathetically-maintained pain, trigeminal neuralgia, dental pain, myofacial pain, phantom-limb pain, bulimia, premenstrual syndrome, premenstrual dysphoric disorder, late luteal phase syndrome, post-traumatic syndrome, chronic fatigue syndrome, urinary incontinence, stress incontinence, urge incontinence, nocturnal incontinence, sexual dysfunction, premature ejaculation, erectile difficulty, erectile dysfunction, premature female orgasm, restless leg syndrome, periodic limb movement disorder, eating disorders, anorexia nervosa, sleep disorders, pervasive developmental disorders, autism, Asperger's disorder, Rett's disorder, childhood disintegrative disorder, learning disabilities, motor skills disorders, mutism, trichotillomania, narcolepsy, post-stroke depression, stroke-induced brain damage, stroke-induced neuronal damage, Gilles de la Tourettes disease, tinnitus, tic disorders, body dysmorphic disorders, oppositional defiant disorder or post-stroke disabilities. In a preferred embodiment, the compounds are considered useful for the treatment, prevention or alleviation of depression.

It is at present contemplated that a suitable dosage of the active pharmaceutical ingredient (API) is within the range of from about 0.1 to about 1000 mg API per day, more preferred of from about 10 to about 500 mg API per day, most preferred of from about 30 to about 100 mg API per day, dependent, however, upon the exact mode of administration, the form in which it is administered, the indication considered, the subject and in particular the body weight of the subject involved, and further the preference and experience of the physician or veterinarian in charge.

Preferred compounds of the invention show a biological activity in the sub-micromolar and micromolar range, i.e. of from below 1 to about 100 μM.

Pharmaceutical Compositions

In another aspect the invention provides novel pharmaceutical compositions comprising a therapeutically effective amount of the chemical compound of the invention.

While a chemical compound of the invention for use in therapy may be administered in the form of the raw chemical compound, it is preferred to introduce the active ingredient, optionally in the form of a physiologically acceptable salt, in a pharmaceutical composition together with one or more adjuvants, excipients, carriers, buffers, diluents, and/or other customary pharmaceutical auxiliaries.

In a preferred embodiment, the invention provides pharmaceutical compositions comprising the chemical compound of the invention, or a pharmaceutically acceptable salt or derivative thereof, together with one or more pharmaceutically acceptable carriers, and, optionally, other therapeutic and/or prophylactic ingredients, known and used in the art. The carrier(s) must be "acceptable" in the sense of being compatible with the other ingredients of the formulation and not harmful to the recipient thereof.

Pharmaceutical compositions of the invention may be those suitable for oral, rectal, bronchial, nasal, pulmonal, topical (including buccal and sub-lingual), transdermal, vaginal or parenteral (including cutaneous, subcutaneous, intramuscular, intraperitoneal, intravenous, intraarterial, intracerebral, intraocular injection or infusion) administration, or those in a form suitable for administration by inhalation or insufflation, including powders and liquid aerosol administration, or by sustained release systems. Suitable examples of sustained release systems include semipermeable matrices of solid hydrophobic polymers containing the compound of the invention, which matrices may be in form of shaped articles, e.g. films or microcapsules.

The chemical compound of the invention, together with a conventional adjuvant, carrier, or diluent, may thus be placed into the form of pharmaceutical compositions and unit dosages thereof. Such forms include solids, and in particular tablets, filled capsules, powder and pellet forms, and liquids, in particular aqueous or non-aqueous solutions, suspensions, emulsions, elixirs, and capsules filled with the same, all for oral use, suppositories for rectal administration, and sterile injectable solutions for parenteral use. Such pharmaceutical compositions and unit dosage forms thereof may comprise conventional ingredients in conventional proportions, with or without additional active compounds or principles, and such unit dosage forms may contain any suitable effective amount of the active ingredient commensurate with the intended daily dosage range to be employed.

The chemical compound of the present invention can be administered in a wide variety of oral and parenteral dosage forms. It will be obvious to those skilled in the art that the following dosage forms may comprise, as the active component, either a chemical compound of the invention or a pharmaceutically acceptable salt of a chemical compound of the invention.

For preparing pharmaceutical compositions from a chemical compound of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavouring agents, solubilizers, lubricants, suspending agents, binders, preservatives, tablet disintegrating agents, or an encapsulating material.

In powders, the carrier is a finely divided solid, which is in a mixture with the finely divided active component.

In tablets, the active component is mixed with the carrier having the necessary binding capacity in suitable proportions and compacted in the shape and size desired.

The powders and tablets preferably contain from five or ten to about seventy percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as carrier providing a capsule in which the active component, with or without carriers, is surrounded by a carrier, which is thus in association with it. Similarly, cachets and lozenges are included. Tablets, powders, capsules, pills, cachets, and lozenges can be used as solid forms suitable for oral administration.

For preparing suppositories, a low melting wax, such as a mixture of fatty acid glyceride or cocoa butter, is first melted and the active component is dispersed homogeneously therein, as by stirring. The molten homogenous mixture is then poured into convenient sized moulds, allowed to cool, and thereby to solidify.

Compositions suitable for vaginal administration may be presented as pessaries, tampons, creams, gels, pastes, foams or sprays containing in addition to the active ingredient such carriers as are known in the art to be appropriate.

Liquid preparations include solutions, suspensions, and emulsions, for example, water or water-propylene glycol solutions. For example, parenteral injection liquid preparations can be formulated as solutions in aqueous polyethylene glycol solution.

The chemical compound according to the present invention may thus be formulated for parenteral administration (e.g. by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, and may contain formulation agents such as suspending, stabilising and/or dispersing agents. Alternatively, the active ingredient may be in powder form, obtained by aseptic isolation of sterile solid or by lyophilization from solution, for constitution with a suitable vehicle, e.g. sterile, pyrogen-free water, before use.

Aqueous solutions suitable for oral use can be prepared by dissolving the active component in water and adding suitable colorants, flavours, stabilising and thickening agents, as desired.

Aqueous suspensions suitable for oral use can be made by dispersing the finely divided active component in water with viscous material, such as natural or synthetic gums, resins, methylcellulose, sodium carboxymethylcellulose, or other well known suspending agents.

Also included are solid form preparations, intended for conversion shortly before use to liquid form preparations for oral administration. Such liquid forms include solutions, suspensions, and emulsions. In addition to the active component such preparations may comprise colorants, flavours, stabilisers, buffers, artificial and natural sweeteners, dispersants, thickeners, solubilizing agents, and the like.

For topical administration to the epidermis the chemical compound of the invention may be formulated as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also contain one or more emulsifying agents, stabilising agents, dispersing agents, suspending agents, thickening agents, or colouring agents.

Compositions suitable for topical administration in the mouth include lozenges comprising the active agent in a flavoured base, usually sucrose and acacia or tragacanth; pastilles comprising the active ingredient in an inert base such as gelatin and glycerine or sucrose and acacia; and mouthwashes comprising the active ingredient in a suitable liquid carrier.

Solutions or suspensions are applied directly to the nasal cavity by conventional means, for example with a dropper, pipette or spray. The compositions may be provided in single or multi-dose form.

Administration to the respiratory tract may also be achieved by means of an aerosol formulation in which the active ingredient is provided in a pressurised pack with a suitable propellant such as a chlorofluorocarbon (CFC) for example dichlorodifluoromethane, trichlorofluoromethane, or dichlorotetrafluoroethane, carbon dioxide, or other suitable gas. The aerosol may conveniently also contain a surfactant such as lecithin. The dose of drug may be controlled by provision of a metered valve.

Alternatively the active ingredients may be provided in the form of a dry powder, for example a powder mix of the compound in a suitable powder base such as lactose, starch, starch derivatives such as hydroxypropylmethyl cellulose and polyvinylpyrrolidone (PVP). Conveniently the powder carrier will form a gel in the nasal cavity. The powder composition may be presented in unit dose form for example in capsules or cartridges of, e.g., gelatin, or blister packs from which the powder may be administered by means of an inhaler.

In compositions intended for administration to the respiratory tract, including intranasal compositions, the compound will generally have a small particle size for example of the order of 5 microns or less. Such a particle size may be obtained by means known in the art, for example by micronization.

When desired, compositions adapted to give sustained release of the active ingredient may be employed.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packaged tablets, capsules, and powders in vials or ampoules. Also, the unit dosage form can be a capsule, tablet, cachet, or lozenge itself, or it can be the appropriate number of any of these in packaged form.

Tablets or capsules for oral administration and liquids for intravenous administration and continuous infusion are preferred compositions.

Further details on techniques for formulation and administration may be found in the latest edition of *Remington's Pharmaceutical Sciences* (Maack Publishing Co., Easton, Pa.).

A therapeutically effective dose refers to that amount of active ingredient, which ameliorates the symptoms or condition. Therapeutic efficacy and toxicity, e.g. $ED_{50}$ and $LD_{50}$, may be determined by standard pharmacological procedures in cell cultures or experimental animals. The dose ratio between therapeutic and toxic effects is the therapeutic index and may be expressed by the ratio $LD_{50}/ED_{50}$. Pharmaceutical compositions exhibiting large therapeutic indexes are preferred.

The dose administered must of course be carefully adjusted to the age, weight and condition of the individual being treated, as well as the route of administration, dosage form and regimen, and the result desired, and the exact dosage should of course be determined by the practitioner.

The actual dosage depends on the nature and severity of the disease being treated, and is within the discretion of the physician, and may be varied by titration of the dosage to the particular circumstances of this invention to produce the desired therapeutic effect. However, it is presently contemplated that pharmaceutical compositions containing of from about 0.1 to about 500 mg of active ingredient per individual dose, preferably of from about 1 to about 100 mg, most preferred of from about 1 to about 10 mg, are suitable for therapeutic treatments.

The active ingredient may be administered in one or several doses per day. A satisfactory result can, in certain instances, be obtained at a dosage as low as 0.1 µg/kg i.v. and 1 µg/kg p.o. The upper limit of the dosage range is presently considered to be about 10 mg/kg i.v. and 100 mg/kg p.o. Preferred ranges are from about 0.1 μg/kg to about 10 mg/kg/day i.v., and from about 1 μg/kg to about 100 mg/kg/day p.o.

Methods of Therapy

In another aspect the invention provides a method for the treatment, prevention or alleviation of a disease or a disorder or a condition of a living animal body, including a human, which disease, disorder or condition is responsive to inhibition of monoamine neurotransmitter re-uptake in the central nervous system, and which method comprises administering to such a living animal body, including a human, in need thereof an effective amount of a chemical compound of the invention.

It is at present contemplated that suitable dosage ranges are 0.1 to 1000 milligrams daily, 10-500 milligrams daily, and especially 30-100 milligrams daily, dependent as usual upon the exact mode of administration, form in which administered, the indication toward which the administration is directed, the subject involved and the body weight of the subject involved, and further the preference and experience of the physician or veterinarian in charge.

EXAMPLES

The invention is further illustrated with reference to the following examples, which are not intended to be in any way limiting to the scope of the invention as claimed.

General: All reactions involving air sensitive reagents or intermediates were performed under nitrogen or argon and in anhydrous solvents.

3,9-Diaza-spiro[5.5]undecane-3-carboxylic acid tert-butyl ester

Was prepared according to Claremont, D. E; Liverton, N and Baldwin; J. J. U.S. Pat. No. 5,451,578, 1995; Chem. Abstr: 1995, 124, 145932.

9-Methyl-3,9-diaza-spiro[5.5]undecane-3-carboxylic acid tert-butyl ester

To an ice cooled solution of 3,9-diaza-spiro[5.5]undecane-3-carboxylic acid tert-butyl ester (1.55 g, 6 mmol) in dichloroethane (50 mL) formaldehyde (0.68 mL, 9 mmol) was added and stirred for 1 h at 0° C. Sodium triacetoxyborohydride (2.54 g, 12 mmol) was added and the reaction stirred at room temperature over night. Aqueous sodium hydrogencarbonate (sat. 50 mL) and water (50 mL) were added and the aqueous phase extracted five times with dichloromethane. The combined organic phase was washed with brine, dried (sodium sulfate), filtered and evaporated. Flash chromatography (dichloromethane/methanol 9:1 with 1% ammonium hydroxide) gave 435 mg (27%) 9-methyl-3,9-diaza-spiro[5.5]undecane-3-carboxylic acid tert-butyl ester.

3-Methyl-3,9-diaza-spiro[5.5]undecane

9-Methyl-3,9-diaza-spiro[5.5]undecane-3-carboxylic acid tert-butyl ester (435 mg, 1.62 mmol) was dissolved in dichloromethane (11 mL) and cooled on ice. Trifluoroacetic acid (4 mL) in dichloromethane (5 mL) was added and the reaction mixture was stirred at room temperature for 2 h. Evaporation to dryness, co-evaporation with toluene, ethyl acetate and diethyl ether gave a foam which was dissolved in dichloromethane and sodium hydroxide (2 N) was added. The aqueous phase was extracted five times with dichloromethane. The combined organic phase was washed with brine, dried (sodium sulfate), filtered and evaporated to give 214 mg (78%) of 3-methyl-3,9-diaza-spiro[5.5]undecane.

Method A 3-(6-Methoxy-naphthalen-2-yl)-3,9-diaza-spiro[5.5]undecane-3-carboxylic acid tert-butyl ester A mixture of 3,9-diaza-spiro[5.5]undecane-3-carboxylic acid tert-butyl ester (500 mg, 1.97 mmol), 2-bromo-6-methoxynaphthalene (934 mg, 3.94 mmol) and sodium tert-butoxide (379 mg, 3.94 mmol) in dry toluene (10 mL) was degassed with argon for 30 min. Palladium(II) acetate (22 mg, 0.1 mmol) and 2,2'-bi(diphenylphosphino)-1,1'-binaphthalene (BINAP) (61.3 mg, 0.2 mmol) were added and the mixture heated to reflux over night. The mixture was filtered and the filtrate evaporated to dryness. Flash chromatography (ethyl acetate/heptane 1:4) gave 666 mg (82%) of 3-(6-methoxy-naphthalen-2-yl)-3,9-diaza-spiro[5.5]undecane-3-carboxylic acid tert-butyl ester.

3-(3,4-Dichloro-phenyl)-9-methyl-3,9-diaza-spiro[5.5]undecane

Was prepared according to method A from 3-methyl-3,9-diaza-spiro[5.5]undecane and 1-bromo-3,4-dichlorobenzene as a yellow oil. LC-ESI–HRMS of [M+H]+ shows 313.1238 Da. Calc. 313.123829 Da, dev. −0.1 ppm.

3-(3,4-Dichloro-phenyl)-3,9-diaza-spiro[5.5]undecane-3-carboxylic cid tert-butyl ester A mixture of 3,9-diaza-spiro[5.5]undecane-3-carboxylic acid tert-butyl ester (1.5 g, 5.9 mmol), 1-bromo-3,4-dichlorobenzene (1.6 g, 7.08 mmol), cesium carbonate (769 mg, 2.36 mmol) and potassium carbonate (981 mg, 7.1 mmol) in dry toluene (50 mL) was degassed with argon for 30 min. Bisdibenzylideneacetone palladium ($Pd_2(dba)_3$) (170 mg, 0.3 mmol) and 2,2'-bi(diphenylphosphino)-1,1'-binaphthalene (BINAP) (367 mg, 0.5 mmol) were added and the mixture heated to reflux over night. The mixture was filtered and the filtrate evaporated to dryness. Flash chromatography (dichloromethane/methanol 9:1 with 1% ammonium hydroxide) gave 431 mg (18%) of 3-(3,4-dichloro-phenyl)-3,9-diaza-spiro[5.5]undecane-3-carboxylic acid tert-butyl ester.

Method B 3-(6-Chloro-pyridin-2-yl)-3,9-diaza-spiro[5.5]undecane-3-carboxylic acid tert-butyl ester 3,9-Diaza-spiro[5.5]undecane-3-carboxylic acid tert-butyl ester (300 mg, 1.18 mmol), 2,6-dichlororpyridine (349 mg, 2.36 mmol) and sodium carbonate (250 mg, 2.35 mmol) in dry toluene were stirred under argon for 30 min. Bisdibenzylideneacetone palladium ($Pd_2(dba)_3$) (4 mg, 0.06 mmol) and 9,9-dimethyl-4,5-bis(diphenyl-phosphino)xanthene (Xantphos) (68 mg, 0.12 mmol) were added and the mixture warmed to reflux overnight. Both bisdibenzylideneacetone palladium ($Pd_2(dba)_3$) (54 mg, 0.06 mmol) and 9,9-dimethyl-4,5-bis(diphenyl-phosphino)xanthene (Xantphos) (68 mg, 0.12 mmol) were added again and the mixture warmed to reflux overnight. The mixture was filtered and the filtrate concentrated in vacuo. Flash chromatography (ethyl acetate/heptane 1:20-1:5) gave 383 mg (84%) of 3-(6-chloro-pyridin-2-yl)-3,9-diaza-spiro[5.5]-undecane-3-carboxylic acid tert-butyl ester.

3-(5-Chloro-pyridin-2-yl)-3,9-diaza-spiro[5.5]undecane-3-carboxylic acid tert-butyl ester Was prepared according to method B from 3,9-diaza-spiro[5.5]undecane-3-carboxylic acid tert-butyl ester and 2,5-dichlororpyridine.

3-(6-Bromo-pyridin-2-yl)-3,9-diaza-spiro[5.5]undecane-3-carboxylic acid tert-butyl ester Was prepared according to method B from 3-methyl-3,9-diaza-spiro[5.5]undecane and 2,6-dibromopyridine and with potassium tert-butoxide instead of sodium carbonate.

9-(4-Chloro-pyridin-2-yl)-9-methyl-3,9-diaza-spiro[5.5]undecane

Was prepared according to method B from 3-methyl-3,9-diaza-spiro[5.5]undecane and 2,6-dichloropyridine. Mp. 204.3-205.4° C.

9-(4-Chloro-phenyl)-3,9-diaza-spiro[5.5]undecane-3-carboxylic acid tert-butyl ester Was prepared according to method B from 3-methyl-3,9-diaza-spiro[5.5]undecane and 4-bromochlorobenzene and with sodium tert-butoxide instead of sodium carbonate.

9-(5-Bromo-pyridin-2-yl)-3,9-diaza-spiro[5.5]undecane-3-carboxylic acid tert-butyl ester Was prepared according to method B from 3-methyl-3,9-diaza-spiro[5.5]undecane and 2,5-dibromopyridine and with sodium tert-butoxide instead of sodium carbonate.

9-(3-Chloro-4-fluoro-phenyl)-3,9-diaza-spiro[5.5]undecane-3-carboxylic acid tert-butyl ester Was prepared according to method B from 3-methyl-3,9-diaza-spiro[5.5]undecane and 4-bromo-2-chlorofluorobenzene and with sodium tert-butoxide instead of sodium carbonate.

9-Naphthalen-2-yl-3,9-diaza-spiro[5.5]undecane-3-carboxylic acid tert-butyl ester Was prepared according to method B from 3-methyl-3,9-diaza-spiro[5.5]undecane and 2-bromonaphtalene and with sodium tert-butoxide instead of sodium carbonate.

3-(2,3-Dichloro-phenyl)-3,9-diaza-spiro[5.5]undecane-3-carboxylic acid tert-butyl ester 3,9-Diaza-spiro[5.5]undecane-3-carboxylic acid tert-butyl ester (500 mg, 1.97 mmol) in dry tetrahydrofuran (4 mL) was cooled to −78° C. n-BuLi (1.6 M in hexanes, 1.28 mL) was added drop-wise. The mixture was stirred for 15 min and 2,3-dichlorofluoro-benzene (324 mg, 2 mmol) in dry tetrahydrofuran (2 mL) was added drop-wise. The mixture was stirred for 15 min. at −78° C. and was then allowed to warm up to room temperature. Aqueous ammonium chloride was added and the aqueous phase extracted three times with ethyl acetate. The combined organic phase was washed with brine, dried (sodium sulfate), filtered and evaporated. Flash chromatography (ethyl acetate/heptane 1:1) gave 266 mg (51%) of 3-(2,3-dichloro-phenyl)-3,9-diaza-spiro[5.5]undecane-3-carboxylic acid tert-butyl ester.

Method C

3-(6-Chloro-pyridin-2-yl)-3,9-diaza-spiro[5.5]undecane fumaric acid salt

To an ice cooled solution of 3-(6-chloro-pyridin-2-yl)-3,9-diaza-spiro[5.5]undecane-3-carboxylic acid tert-butyl ester (380 mg, 1.04 mmol) in dichloromethane (4 mL) trifluoroacetic acid (2 mL in 4 mL dichloromethane) was added. The mixture was stirred for 1 h and sodium hydroxide (1 N) was added and the aqueous phase extracted six times with dichloromethane. Drying (sodium sulfate) filtration and evaporation gave the crude product. Fumaric acid in diethyl ether/methanol 9:1 gave 283 mg (100%) of 3-(6-chloro-pyridin-2-yl)-3,9-diaza-spiro[5.5]undecane fumaric acid salt as a with solid. Decomposes above 250° C.

3-(5-Chloro-pyridin-2-yl)-3,9-diaza-spiro[5.5]undecane

Was prepared according to method C from 3-(5-chloro-pyridin-2-yl)-3,9-diaza-spiro[5.5]undecane-3-carboxylic acid tert-butyl ester. Mp. 71.2-72.9° C.

3-(6-Methoxy-naphthalen-2-yl)-3,9-diaza-spiro[5.5]undecane

Was prepared according to method C from 3-(6-methoxy-naphthalen-2-yl)-3,9-diaza-spiro[5.5]undecane-3-carboxylic acid tert-butyl ester as the free base. Mp. 175.8-177.6° C.

3-(3,4-Dichloro-phenyl)-3,9-diaza-spiro[5.5]undecane

Was prepared according to method C from 3-(3,4-dichloro-phenyl)-3,9-diaza-spiro[5.5]undecane-3-carboxylic acid tert-butyl ester as the free base. Mp. 209-212° C.

3-(6-Bromo-pyridin-2-yl)-3,9-diaza-spiro[5.5]undecane fumaric acid salt

Was prepared according to method C from 3-(6-bromo-pyridin-2-yl)-3,9-diaza-spiro[5.5]undecane-3-carboxylic acid tert-butyl ester as the fumaric acid salt. Mp. 198.5-199.3° C.

3-(2,3-Dichloro-phenyl)-3,9-diaza-spiro[5.5]undecane

Was prepared according to method C from 3-(2,3-dichloro-phenyl)-3,9-diaza-spiro[5.5]undecane-3-carboxylic acid tert-butyl ester as the free base. Mp. 80.4-81.9° C.

3-(4-Chloro-phenyl)-3,9-diaza-spiro[5.5]undecane

Was prepared according to method C from 9-(4-chloro-phenyl)-3,9-diaza-spiro[5.5]undecane-3-carboxylic acid tert-butyl ester as the free base. Mp. 95.5-97.4° C.

3-(3-Chloro-4-fluoro-phenyl)-3,9-diaza-spiro[5.5]undecane fumaric acid salt

Was prepared according to method C from 9-(3-chloro-4-fluoro-phenyl)-3,9-diaza-spiro[5.5]undecane-3-carboxylic acid tert-butyl ester as the fumaric acid salt. Mp. 201.4-202.2° C.

3-(5-Bromo-pyridin-2-yl)-3,9-diaza-spiro[5.5]undecane

Was prepared according to method C from 9-(5-bromo-pyridin-2-yl)-3,9-diaza-spiro-[5.5]undecane-3-carboxylic acid tert-butyl ester as the free base. Mp. 103-105° C.

3-Naphthalen-2-yl-3,9-diaza-spiro[5.5]undecane

Was prepared according to method C from 9-naphthalen-2-yl-3,9-diaza-spiro[5.5]undecane-3-carboxylic acid tert-butyl ester as the free base. Mp. 158-162° C.

3-(6-Methoxy-naphthalen-2-yl)-9-methyl-3,9-diaza-spiro[5.5]undecane

To an ice cooled solution of 3-(6-methoxy-naphthalen-2-yl)-3,9-diaza-spiro[5.5]-undecane (294 mg, 0.95 mmol) in dichloroethane (20 mL), formaldehyde (37% in water, 204 µL, 2.84 mmol) was added and stirred for 1 h at 0° C. Sodium triacetoxyborohydride (402 mg, 1.89 mmol) was added and stirred at room temperature over night. The reaction was quenched with aqueous sodium hydrogencarbonate (sat.) and evaporated. The remaining aqueous phase was extracted three times with dichloromethane and the combined organic phase was dried (sodium sulfate), filtered and evaporated to give 270 mg (80%) of 3-(6-methoxy-naphthalen-2-yl)-9-methyl-3,9-diaza-spiro[5.5]undecane. Mp. 122.2-124.9° C.

TEST EXAMPLE

In vitro Inhibition Activity

A number of compounds were tested for their ability to inhibit the reuptake of the monoamine neurotransmitters dopamine (DA) noradrenaline (NA) and serotonine (5-HT) in synaptosomes as described in WO 97/16451.

The test values are given as $IC_{50}$ (the concentration (µM) of the test substance which inhibits the specific binding of $^3$H-DA, $^3$H-NA, or $^3$H-5-HT by 50%).

Test results obtained by testing selected compounds of the present invention appear from the below table:

TABLE 1

| Test compound | DA-uptake $IC_{50}$ (82 M) | NA-uptake $IC_{50}$ (82 M) | 5-HT-uptake $IC_{50}$ (82 M) |
|---|---|---|---|
| $3^{rd}$ compound of method C; 3-(6-Methoxy-naphthalen-2-yl)-3,9-diaza-spiro[5.5]undecane | 0.45 | 0.55 | 0.080 |
| $4^{th}$ compound of method C; 3-(3,4-Dichloro-phenyl)-3,9-diaza-spiro[5.5]undecane | 0.96 | 0.56 | 0.0034 |
| $7^{th}$ compound of method C; 3-(4-Chloro-phenyl)-3,9-diaza-spiro[5.5]undecane | 1.4 | 1.2 | 0.0084 |

The invention claimed is:
1. A compound of Formula I:

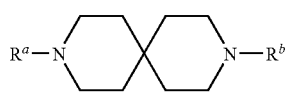

(I)

any of its stereoisomers or any mixture of its stereoisomers, or a pharmaceutically acceptable salt thereof;

wherein
$R^a$ represents hydrogen or alkyl;
which alkyl is optionally substituted with one or more substituents independently selected from the group consisting of:
halo, trifluoromethyl, trifluoromethoxy, cyano, hydroxy, amino, nitro, alkoxy, cycloalkoxy, alkyl, cycloalkyl, cycloalkylalkyl, alkenyl and alkynyl; and
$R^b$ represents an aryl or a heteroaryl group;
which aryl or heteroaryl group group is optionally substituted with one or more substituents independently selected from the group consisting of:
halo, trifluoromethyl, trifluoromethoxy, cyano, nitro, hydroxy, alkoxy, cycloalkoxy, alkoxyalkyl, cycloalkoxyalkyl, methylenedioxy, ethylenedioxy, alkyl, cycloalkyl, cycloalkylalkyl, alkenyl, alkynyl, —NR'R", —(C═O)NR'R" or —NR'(C═O)R";
wherein R' and R" independent of each other are hydrogen or alkyl;
with the proviso that the compound is not
4-(3,9-diaza-spiro[5.5]undec-3-yl)-benzonitrile or
3-pyridin-4-yl-3,9-diaza-spiro[5.5]undecane.
2. The compound of claim 1, or a pharmaceutically acceptable salt thereof, wherein
$R^a$ represents hydrogen or alkyl.
3. The compound of claim 1, or a pharmaceutically acceptable salt thereof, wherein
$R^b$ represents a phenyl group,
which phenyl group is optionally substituted with one or more substituents independently selected from the group consisting of:
halo, trifluoromethyl, trifluoromethoxy, cyano arid alkoxy.
4. The compound of claim 1, or a pharmaceutically acceptable salt thereof, wherein
$R^b$ represents a phenyl group,
which phenyl group is substituted twice with substituents independently selected from the group consisting of:
halo, trifluoromethyl, trifluoromethoxy, cyano and alkoxy.
5. The compound of claim 1, or a pharmaceutically acceptable salt thereof, wherein
$R^b$ represents a naphthyl group,
which naphthyl group is optionally substituted with one or more substituents independently selected from the group consisting of:
halo, trifluoromethyl, trifluoromethoxy, cyano and alkoxy.
6. The compound of claim 1, or a pharmaceutically acceptable salt thereof, wherein
$R^b$ represents a pyridyl group,
which pyridyl group is optionally substituted with one or more substituents independently selected from the group consisting of:
halo, trifluoromethyl, trifluoromethoxy, cyano arid alkoxy.
7. The compound of claim 1, which is
3-(3,4-Dichloro-phenyl)-9-methyl-3,9-diaza-spiro[5.5]undecane;
3-(6-Chloro-pyridin-2-yl)-9-methyl-3,9-diaza-spiro[5.5]undecane;
3-(6-Chloro-pyridin-2-yl)-3,9-diaza-spiro[5.5]undecane;
3-(5-Chloro-pyridin-2-yl)-3,9-diaza-spiro[5.5]undecane;
3-(6-Methoxy-naphthalen-2-yl)-3,9-diaza-spiro[5.5]undecane;
3-(3,4-Dichloro-phenyl)-3,9-diaza-spiro[5.5]undecane;
3-(6-Bromo-pyridin-2-yl)-3,9-diaza-spiro[5.5]undecane;
3-(2,3-Dichloro-phenyl)-3,9-diaza-spiro[5.5]undecane;
3-(4-Chloro-phenyl)-3,9-diaza-spiro[5.5]undecane;

3-(3-Chloro-4-fluoro-phenyl)-3,9-diaza-spiro[5.5]undecane;
3-(5-Bromo-pyridin-2-yl)-3,9-diaza-spiro[5.5]undecane;
3-Naphthalen-2-yl-3,9-diaza-spiro[5.5]undecane;
3-(6-Methoxy-naphthalen-2-yl)-9-methyl-3,9-diaza-spiro[5.5]undecane;
or a pharmaceutically acceptable salt thereof.

8. A pharmaceutical composition, comprising:
a therapeutically effective amount of a compound of Formula I:

(I)

wherein
R$^a$ represents hydrogen or alkyl;
  which alkyl is optionally substituted with one or more substituents independently selected from the group consisting of:
    halo, trifluoromethyl, trifluoromethoxy, cyano, hydroxy, amino, nitro, alkoxy, cycloalkoxy, alkyl, cycloalkyl, cycloalkylalkyl, alkenyl and alkynyl; and
R$^b$ represents an aryl or a heteroaryl group;
  which aryl or heteroaryl group group is optionally substituted with one or more substituents independently selected from the group consisting of:
    halo, trifluoromethyl, trifluoromethoxy, cyano, nitro, hydroxy, alkoxy, cycloalkoxy, alkoxyalkyl, cycloalkoxyalkyl, methylenedioxy, ethylenedioxy, alkyl, cycloalkyl, cycloalkylalkyl, alkenyl, alkynyl, —NR'R", —(C═O)NR'R" or —NR'(C═O)R";
    wherein R' and R" independent of each other are hydrogen or alkyl;
with the proviso that the compound is not 4-(3,9-diaza-spiro[5.5]undec-3-yl)-benzonitrile or
3-pyridin-4-yl-3,9-diaza-spiro[5.5]undecane,
  any of its stereoisomers or any mixture of its stereoisomers, or a pharmaceutically acceptable salt thereof; and
  at least one pharmaceutically acceptable carrier, excipient or diluent.

9. The compound 3-(3,4-Dichlorophenyl)-3,9-diaza-spiro[5.5]undecane or a pharmaceutically acceptable salt thereof.

10. A pharmaceutical composition, comprising:
a therapeutically effective amount of said compound of claim 9 or a pharmaceutically acceptable salt thereof; and
a pharmaceutically acceptable carrier.

11. A method for treating depression, which comprises:
administering to a subject in need thereof an effective amount to treat depression of the composition of claim 8, wherein R$^b$ represents an aryl group or a substituted aryl group.

12. A method for treatment of depression in a human which comprises the step of:
administering to a human in need thereof a therapeutically effective amount of the compound 3-(3,4-Dichlorophenyl)-3,9-diaza-spiro[5.5]undecane or a pharmaceutically acceptable salt thereof.

* * * * *